United States Patent
Samson et al.

[11] Patent Number: 6,090,099
[45] Date of Patent: *Jul. 18, 2000

[54] MULTI-LAYER DISTAL CATHETER SECTION

[75] Inventors: Gene Samson, Milpitas; Kim Nguyen, San Jose, both of Calif.

[73] Assignee: Target Therapeutics, Inc., Fremont, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/653,602

[22] Filed: May 24, 1996

[51] Int. Cl.$^7$ ................................................. A61M 25/00
[52] U.S. Cl. ........................ 604/527; 604/523; 604/524; 604/264
[58] Field of Search ....................... 604/280, 282, 604/264, 265, 281, 523, 524, 527

[56] References Cited

U.S. PATENT DOCUMENTS

| | | |
|---|---|---|
| 2,437,542 | 3/1948 | Krippendorf . |
| 3,174,851 | 3/1965 | Buehler et al. . |
| 3,351,463 | 11/1967 | Rozner et al. . |
| 3,416,531 | 12/1968 | Edwards . |
| 3,753,700 | 8/1973 | Harrison et al. . |
| 4,425,919 | 1/1984 | Alston, Jr. et al. ........... 128/658 |
| 4,484,586 | 11/1984 | McMickle et al. . |
| 4,516,972 | 5/1985 | Samson . |
| 4,636,346 | 1/1987 | Gold et al. . |
| 4,705,511 | 11/1987 | Kocak . |
| 4,739,768 | 4/1988 | Engelson . |
| 4,806,182 | 2/1989 | Rydell et al. . |
| 4,832,681 | 5/1989 | Lenck . |
| 4,840,622 | 6/1989 | Hardy . |
| 4,863,442 | 9/1989 | DeMello et al. . |
| 4,994,069 | 2/1991 | Ritchart et al. . |
| 5,037,404 | 8/1991 | Gold et al. . |
| 5,069,674 | 12/1991 | Fearnot et al. . |
| 5,078,702 | 1/1992 | Pomeranz . |
| 5,122,136 | 6/1992 | Guglielmi et al. . |
| 5,176,660 | 1/1993 | Truckai . |
| 5,178,158 | 1/1993 | de Toledo . |
| 5,217,482 | 6/1993 | Keith . |
| 5,221,270 | 6/1993 | Parker ........................... 604/282 |
| 5,226,911 | 7/1993 | Chee et al. . |
| 5,250,071 | 10/1993 | Palermo . |
| 5,254,107 | 10/1993 | Soltesz ........................... 604/282 |
| 5,261,916 | 11/1993 | Engelson . |
| 5,279,596 | 1/1994 | Castaneda et al. . |
| 5,304,194 | 4/1994 | Chee et al. . |
| 5,304,195 | 4/1994 | Twyford, Jr. et al. . |
| 5,312,415 | 5/1994 | Palermo . |
| 5,454,795 | 10/1995 | Samson . |
| 5,462,523 | 10/1995 | Samson et al. ................... 604/30 |
| 5,496,294 | 3/1996 | Hergenrother et al. ........... 604/282 |
| 5,702,373 | 12/1997 | Samson ........................... 604/282 |
| 5,759,173 | 6/1998 | Preissman et al. ................. 604/96 |
| 5,792,124 | 8/1998 | Horrigan et al. .................. 604/282 |
| 5,836,926 | 11/1998 | Peterson et al. ................... 604/282 |
| 5,851,203 | 12/1998 | Va Muiden ........................ 604/282 |
| 5,868,718 | 2/1999 | Pepin et al. ....................... 604/264 |
| 5,891,112 | 4/1999 | Samson ........................... 604/282 |
| 5,906,605 | 5/1999 | Coxum ............................ 604/525 |
| 5,906,606 | 5/1999 | Chee et al. ........................ 604/527 |

FOREIGN PATENT DOCUMENTS

| | | |
|---|---|---|
| 0594201 | 4/1994 | European Pat. Off. . |
| WO 95/13110 | 5/1995 | WIPO . |
| WO 96/33763 | 10/1996 | WIPO . |

*Primary Examiner*—Corrine McDermott
*Assistant Examiner*—Cris L. Rodriguez
*Attorney, Agent, or Firm*—Morrison & Foerster LLP

[57] ABSTRACT

This is a distal-most section of a catheter suitable for treating a tissue target within the body, which target is accessible through the vascular system. Central to the invention is a multi-component or multi-layer catheter section used distally on an endovascular catheter. In particular, the inventive catheter section has at least one interior stiffener member and an exterior tubing member. Between the at least one interior stiffener member and the exterior tubing member is a metallic braid.

9 Claims, 2 Drawing Sheets

MULTI-LAYER DISTAL CATHETER SECTION

FIELD OF THE INVENTION

This invention is a surgical device. In particular, it is the distal-most section of a catheter suitable for treating a tissue target within the body, which target is accessible through the vascular system. Central to the invention is its multi-component or multi-layer structure. In particular, the inventive catheter section has at least one interior stiffener member and an exterior tubing member. Between the at least one interior stiffener member and the exterior tubing member is a metallic braid. The inventive distal section is typically used in conjunction with a catheter having more proximal sections which consist essentially of or comprise polymeric members.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially useful. For instance, it is commonplace to treat diseases of the circulatory system via angioplasty (PTA) using catheters having balloons on their distal tips. It is similarly common that those catheters are used to deliver a radio-opaque agent to that site prior to the PTA procedure to allow viewing of the problem prior to treatment.

Often the target which one desires to access by catheter is within a soft tissue such as the liver or the brain. The difficulty in reaching such a site must be apparent even to the casual observer. The catheter must be introduced through a large artery such as those found in the groin or the neck and be passed through ever narrower regions of the arterial system until the catheter reaches a selected site. Often such pathways will wind back upon themselves in a multi-looped path. These catheters are difficult to design and use in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above. Yet, at the same time, the catheter must not cause significant trauma to the blood vessel or other surrounding tissue. Further details on the problems and an early, but yet effective, way of designing a catheter for such a traversal may be found in U.S. Pat. No. 4,739,768, to Engelson. The Engelson catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along the guidewire once the proper path is established.

There are other ways of causing a catheter to proceed through the human vasculature to a selected site, but a guidewire-aided catheter is considered to be both quite quick and somewhat more accurate than the other procedures.

Once the guidewire and the catheter reach the chosen target, the guidewire is typically then removed so to allow treatment or diagnostic procedures to begin. This invention is especially suitable for placement of vaso-occlusive devices. These treatment devices have been known to hang within the lumens of catheters not having special provisions to assure that those inner lumen are generally obstruction-free.

Typical of the vaso-occlusive devices suitable for use with this catheter are those found in U.S. Pat. No. 4,994,069, to Ritchart et al, (vaso-occlusive coils); U.S. Pat. No. 5,122,136, to Guglielmi et al (electrolytically detachable vaso-occlusive coils); U.S. Pat. No. 5,226,911 and 5,304,194, to Chee et al (vaso-occlusive coils with attached fibers); U.S. Pat. No. 5,250,071, to Palermo (mechanically detachable coils); U.S. Pat. No. 5,261,916, to Engelson (mechanically detachable coil); U.S. Pat. No. 5,304,195, to Twyford et al (mechanically detachable coils); and U.S. Pat. No. 5,312,415, to Palermo (mechanically detachable coils); the entirety of which are incorporated by reference. These devices each have a relatively rigid diameter and must be pushed through the lumen of the delivery catheter.

Modest kinks (or even "ovalization") in the smaller diameter lumens found in the distal regions of the catheter may cause major problems with delivery due either to the creation of large areas of physical interference in the lumen or simply to the contribution of excessive sliding friction because of the distorted lumen. The creation of relatively kink-free distal interior regions is the goal of this invention. We have found that use of a braided metallic tube located between interior and exterior tubing components in that distal region garners excellent kink resistance without raising the distal section stiffness to an unacceptable level.

Ribbons have been used in winding a catheter body to help prevent kinking. Examples of previously disclosed catheters include U.S. Pat. No. 2,437,542, to Krippendorf. Krippendorf describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet still able to flex in the axial direction. The thus-plasticized tubing is then dipped in some other medium to allow the formation of a flexible varnish of material such as a tung oil base or a phenolic resin and a suitable plasticizer. There is no indication that this device is of the flexibility required herein. Additionally, it appears to be the type which is used in some region other than in the periphery or in soft tissues of the body.

Similarly, U.S. Pat. No. 3,416,531, to Edwards, shows a catheter having braiding-edge walls. The device further has layers of other polymers such as TEFLON and the like. The strands found in the braiding in the walls appear to be threads having classic circular cross-sections. Furthermore, the device is shown to be fairly stiff in that it is designed so that it may be bent using a fairly large handle at its proximal end.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is made of, preferably, an annealed copper wire which has been coated with a body-compatible polymer such as a polyurethane or a silicone. The copper wire is coated and then used in a device which winds the wire into a tube. The wound substrate is then coated with another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is an aramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use as a guidewire.

U.S. Pat. No. 4,705,511, to Kocak, shows an introducer sheath assembly having a helically spaced coil or braid placed within the wall of the device. The disclosed device is shown to be quite stiff, in that it is intended to support other catheters during their introduction in to the human body.

U.S. Pat. No. 4,806,182, to Rydell et al., shows a device using stainless steel braid imbedded in its wall and an inner layer of a polyfluorocarbon. The process also described therein is a way to laminate the polyfluorocarbon onto a polyurethane inner liner so as prevent delamination.

U.S. Pat. No. 4,832,681, to Lenck, shows a method and apparatus for artificial fertilization. The device itself is a long portion of tubing which, depending upon its specific materials of construction, may be made somewhat stiffer by the addition of spiral reinforcement comprising stainless steel wire.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,069,674 shows a small diameter epidural catheter which is flexible and kink-resistant when flexed. The wall has a composite structure including a helical coil, typically stainless steel or the like, a tubular sheath typically of a polymer, and a safety wire which is spiraled about the coil and is often in the shape of a ribbon.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches.

U.S. Pat. No. 5,178,158, to de Toledo, shows a device which is a convertible wire having use either as a guidewire or as a catheter. The coil appears to be a ribbon which forms an internal passage through the coil/catheter device. No interior coating is applied.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

U.S. Pat. No. 5,279,596, to Castaneda et al, suggests the use of an embedded coil in the distal region of an angioplasty or angiography catheter to improve its kink-resistance. However, the patent discloses neither the use of high-elasticity alloys in the coil nor does it suggest the use of the resulting catheters as the vehicles for vaso-occlusive device delivery.

Similarly, multi-layer catheter sections are not, in and of themselves, unique.

U.S. Pat. No. 4,636,346, to Gold et al., shows a thin wall guiding catheter having a distal end which is adapted to be formed into a curved configuration and passed through various branching blood vessels or the like. It has a lubricious inner sheath, a rigid intermediate sheath, and a flexible outer sheath. The distal tip itself is of similar construction but the rigid intermediate sheath is sometimes omitted.

U.S. Pat. No. 4,840,622, to Hardy, shows a cannula which, again, is a multi-layer device used to direct another catheter from the exterior of a human body to some, typically, known position within the human body.

U.S. Pat. No. 4,863,442, to DeMello et al., shows a guide catheter having a tubular body with a wire-braided TEFLON core in a polyurethane jacket. The distal end of the jacket is removed form the core and a soft polyurethane tip is applied to the core over the region where the jacket has been removed. This results in a generally soft tipped but fairly stiff catheter made up of multiple layers.

U.S. Pat. No. 5,078,702, to Pomeranz, shows a soft tip catheter, typically a guide catheter, having multiple sections of varying materials and inner and outer sheaths making up the catheter shaft. However, the intent of Pomeranz is not to produce a catheter having kink resistance, it is instead to form a soft catheter having significant stiffness. It should be noted that the material used in the inner sheath is said to be of a fairly rigid polymer (see column 4).

None of these devices are documents describe catheters having the construction described below.

SUMMARY OF THE INVENTION

This invention is a catheter section made up, desirably, of an outer tubing component and at least one inner stiffener component placed coaxially within that outer tubing component. Between the at least one inner stiffener component and the outer tubing component is a metallic braided tubing member. The outer tubing is desirably of a highly flexible material, most desirably a low density polyethylene (LDPE) or its blend or linear low density polyethylene (LLDPE) which is or has been shrunk wrapped onto the metallic braided tubing member. The most preferred "blend" is of ethylenevinylacetate (EVA) and low density polyethylene (LDPE). The at least one inner tubing component most desirably is a blend of ethylenevinylacetate (EVA) and low density polyethylene (LDPE) or linear low density polyethylene (LLDPE). Tubing constructed of these materials are highly flexible and yet have sufficient wall strength to withstand catheter pressurization without substantial radial strain.

The catheter may be lined or coated with a hydrophilic polymer or other lubricious polymer or it may be lined with a thin layer of a lubricious polymer such as a polytetrafluoroethylene or other polyfluorocarbon.

The catheter section may be included into an integral catheter assembly. Most preferred are more proximal sections which consist essentially of or comprise polymeric tubing. Wise choices of materials permit the catheter to be of a smaller overall diameter than similar catheters currently in use.

DESCRIPTION OF THE INVENTION

This invention is a kink-resistant catheter section and catheter incorporating such a section. It is a composite section including an outer covering with an inner stiffener. A metallic braid is situated between the outer covering and inner stiffener.

Figure 1:
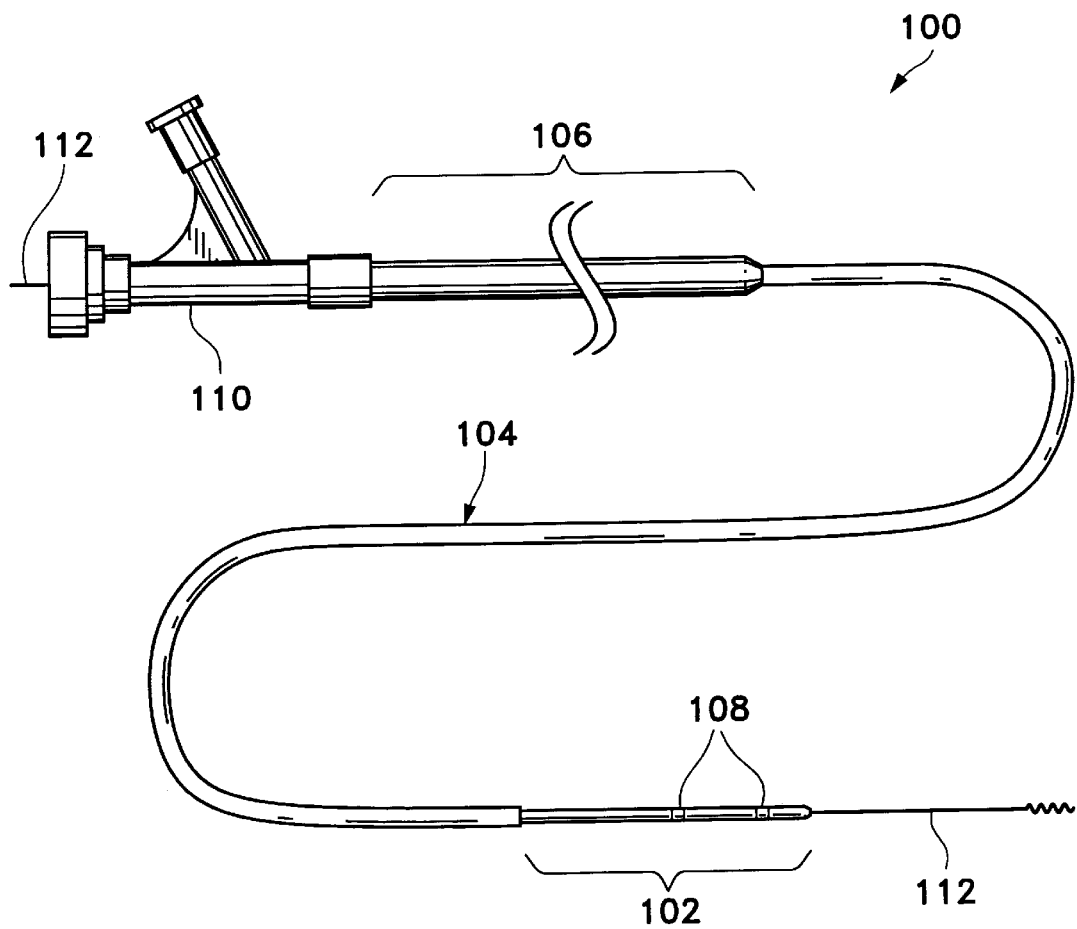
FIG. 1 shows, in side view, a typical three section catheter which may incorporate the distal section of the invention.

A typical multi-section catheter (100) which may incorporate the concepts of this invention is shown in FIG. 1. Such a catheter is described in more detail in U.S. Pat. No. 4,739,768, to Engelson, (the entirety of which is incorporated by reference) and is suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so, since the longer catheters must reach ever more distal and, hence, smaller vascular areas. This smaller diameter requires a concomitant thinning of the wall section. The thinner section walls may kink or ripple when actively pushed along the guidewire or when placed in a curved vessel or when the noted vaso-occlusive devices are pushed through the catheter's lumen. The typical configuration shown in FIG. 1 has a distal section (102) having significant flexibility, an intermediate section (104) which is typically less flexible, and a long proximal section (106) which in turn is least flexible. The distal section (102) is flexible and soft to allow deep penetration into the extraordinary convolutions of the neurological vasculature without trauma. Various known and necessary accessories to the catheter assembly, e.g., one or more radio-opaque bands (108) at the distal region to allow viewing of the position of the distal region under fluoroscopy and a luer assembly (110) for guidewire (112) and fluids access, are also shown in FIG. 1. The typical dimensions of this catheter are:

Overall length: 60–200 cm
Proximal Section (106): 60–150 cm
Intermediate Section (104): 20–50 cm
Distal Section (102): 2.5–30 cm Obviously, these dimensions are not particularly critical to this invention and are selected variously as a function of the malady treated and its site within the body.

The section described in detail below is preferably used in catheters which are polymeric. That is to say that the more proximal sections, e.g., sections 104 and 106 in FIG. 1, consist essentially of polymeric material or at least comprise polymeric material. This limitation is for the purpose of excluding more proximal sections having braids or coils as stiffening means.

Figure 2:
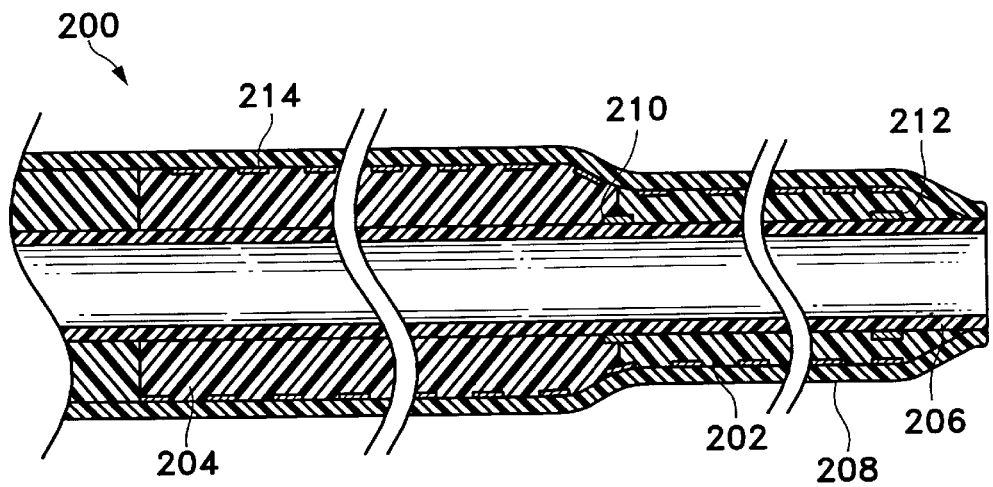
FIGS. 2 and 3 show, in magnification, fragmentary cross-sections of catheter sections made according to this invention.

FIG. 2 shows a magnified partial cross-section of a catheter section (200) showing the aspects of one variation of the invention particularly useful as the distal section of a catheter. This section is very thin, e.g., in having a diameter less than about 0.038 inches, preferably less than about 0.025 inches. In any event, it is sufficiently thin and flexible to access inner regions of the human brain. As shown in FIG. 2, the catheter body or section (200) has a pair of inner tubing stiffener members (202 and 204), an optional lubricious sheath (206), and the outer polymeric layer (208). Also shown are a pair of radio-opaque bands, the proximal band is (210) and the distal band is (212.) Most important to this invention is the braided tubing member (214). The inner tubing stiffening members or inner stiffening tubing sections (202 and 204) desirably are simple sections of tubing which have been cut to length for placement in the catheter section.

The distal inner stiffening tubing section (202) preferably is fairly thin, e.g., 0.0005 to 0.0015 inches in wall thickness. The length of the distal inner stiffening tubing section (202) is typically no more than about 10 to 15 cm. in length although the length is only critical in particular and specific catheter designs. That is to say that a catheter designed for deep access in the brain would involve a distal inner tubing section which is longer than one used for shallower access. The more proximal inner tubing stiffening section (204) is of a similar axial length although the wall thickness is often more than about 2 to 3 times as thick. The inner stiffener members sections, or layers (202 and 204) may be of a wide variety of materials but preferably are LLDPE or LDPE, perhaps containing a small amount of ethylene vinyl acetate (EVA).

The optional inner tubing member or inner liner, also called herein a "lubricious sheath" (206) may be of any of a variety of lubricious polymers, e.g., polytetrafluoroethylene, FEP, or other fluorocarbon polymers or polysulfones. The optional inner liner (206) should not be any thicker than about 0.0005" in wall thickness so to preserve the flexibility of the distal section (200).

The outer layer or outer polymeric layer (208) may also be made of any of a wide variety of materials. These materials include polyurethanes, polyvinylchloride, LDPE, LLDPE, or mixtures of these, but preferably the outer layer (208) is a heat shrinkable tubing of LDPE or LLDPE, having an EVA content of at least 10% EVA, preferably 12 to 20% and a wall thickness of 0.005 to 0.010 inches, preferably about 0.003 inches. These polymers may be crosslinked by radiation to increase their strength and allow heat shrinking.

It should also be noted that each of the polymers discussed herein may be used in conjunction with radio-opaque materials (used as fillers) such as barium sulfate, bismuth trioxide, bismuth carbonate, powdered tungsten, powdered tantalum, or the like so that the location of the various pieces of tubing may be radiographically visualized within the vessel. A tradeoff in adding such powdered fillers to the polymeric mix is decreased flexibility of the resulting catheter assembly, however.

Also shown in FIG. 2 is a pair of radio-opaque markers (210 & 212). These markers (210 & 212) may be made of platinum or other suitably radio-opaque material so to allow the physician using the catheter to radiographically visualize the position of the catheter's distal tip when it is present in the body. The proximal marker (210) is usually considered to be optional for most applications.

Central to this invention is the presence of the braid between the inner tubing stiffener members (202 & 204) and outer covering (208).

Figure 3:
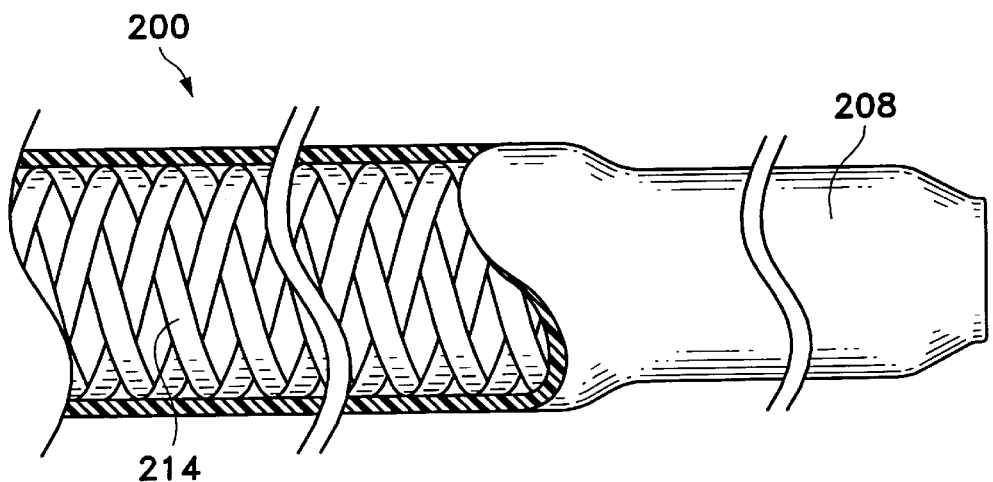

The metallic braid (214) shown both in FIGS. 2 and 3 is made up of a number of metallic ribbons. A majority of the metallic ribbons in braid (214) are most desirably of members of a class of alloys known as superelastic alloys.

Preferred super-elastic alloys include the class of titanium/nickel materials known as nitinol—alloys discovered by the U.S. Navy Ordnance Laboratory. These materials are discussed at length in U.S. Pat. No. 3,174,851 to Buehler et al., U.S. Pat. No. 3,351,463 to Rozner et al., and U.S. Pat. No. 3,753,700 to Harrison et al. Commercial alloys containing up to about 5% of one or more other members of the iron group, e.g., Fe, Cr, Co, are considered to be encompassed within the class of superelastic Ni/Ti alloys suitable for this service.

When using a superelastic alloy, an additional step may be desirable to preserve the shape of the stiffening braid. For instance, with a Cr-containing Ni/Ti superelastic alloy which has been rolled into a 1×4 mil ribbon and formed into a 16-member braid, some heat treatment is desirable. The braid is placed onto a mandrel, usually metallic, of an appropriate size. The braid is then heated to a temperature of 650°–750° F. for a few minutes, possibly (but not necessarily) annealing the constituent ribbon. After heat treatment, the braid retains its shape and the alloy retains its superelastic properties.

Metallic ribbons that are suitable for use in the braid (214) of this invention are desirably between 0.00025 and 0.0035 inches in thickness and 0.0025 and 0.012 inches in width. By the term "ribbon", I intend to include elongated shapes, the cross-section of which are not square or round and may typically be rectangular, oval or semi-oval. They should have an aspect ratio of at least 0.5 (thickness/width). In any event, for superelastic alloys, particularly nitinol, the thickness and width may be somewhat finer, e.g., down to 0.0.00030 and 0.001 inches, respectively. Currently available ribbons include sizes of 0.001×0.003, 0.001×0.004 inches, 0.002×0.006 inches, and 0.002×0.008 inches.

The ribbons making up the braid (214) shown in FIGS. 2 and 3 may also contain an amount of non-superelastic materials. Although metallic ribbons are preferred as the ancillary materials because of their strength-to-weight ratios, fibrous materials (both synthetic and natural) may also be used. Preferred, because of cost, strength, and ready availability are stainless steels (SS308, SS304, SS318, etc.) and tungsten alloys. In certain applications, particularly smaller diameter catheter sections, more malleable metals and alloys, e.g., gold, platinum, palladium, rhodium, etc. may be used. A platinum alloy with a few percent of tungsten is preferred partially because of its radio-opacity.

Suitable non-metallic ribbons include high performance materials such as those made of polyaramids (e.g., KEVLAR) and carbon fibers.

The braids utilized in this invention may be made using commercially available tubular braiders. Whenever I use the term "braid" herein, I mean tubular constructions in which the ribbons making up the construction are woven in an in-and-out fashion as they cross to form a tubular member defining a single lumen. The braids may be made up of a suitable number of ribbons, typically six or more. Ease of production on a commercial braider typically results in braids having eight or sixteen ribbons.

The braid shown in FIGS. 2 and 3 has a nominal pitch angle of 45°. Clearly the invention is not so limited. Other braid angles from 20° to 60° are also suitable. An important variation of this invention is the ability to vary the pitch angle of the braid either at the time the braid is woven or at the time the braid is included in the catheter section or sections.

FIGS. 2 and 3 show a variation of the invention in which the catheter section (200) has two portions of different diameter. The larger diameter portion may utilize a braid with one nominal braid angle and the smaller diameter portion may have a different braid angle. This diminution in catheter diameter may be accomplished in a number of different ways. As noted above, the inner liner sections (202 and 204) may be sized with two different diameters in the respected different portions of the catheter section (200). The braid (214) may then be stretched axially as it is placed upon that liner. When the outer covering or outer layer (208) is placed on the braid (214), the braid (214) will retain its multi-diameter configuration. This variation has the benefit of being quite simple in construction and yet provides a variety of different flexibilities to the catheter section without a significant change in the materials of construction.

The inventive catheter section (200) may be constructed of a braid (214) constructed of ribbons of different width. For instance, the braid may be wound using a wide ribbon and a narrower ribbon. It is desirable to balance the size and types of ribbons woven in each direction. As also noted above, these various ribbons should be, in the main, superelastic alloy. However, they may be fibrous materials such as polyaramids (e.g., Kevlar) or materials of other metals or alloys such as stainless steel. However, to accomplish the benefits of the invention, the major portion of the ribbons making up a braid should be superelastic alloy.

The variations shown above have each shown a single-ribbon wind. Single-ribbon winds permit the braid to contain the maximum amount of open area between ribbons in the braid. However, the catheter section need not be made with a single wind. The braid (214) may be woven using a double-ribbon wind. In this variation, a pair of ribbons is placed side by side and treated as shown in the single ribbon variation described in FIGS. 2–3 above. This variation produces a braid which is denser than the single-ribbon wind. Typically, the regions between adjacent winds are smaller. The invention described herein is intended to encompass multiple-wind braids. However, some of the benefits of the invention are diminished as the density of the ribbons in the catheter section is increased. That is to say that the stiffness of the catheter section substantially increases as the number of ribbons used in a multiple-ribbon weave is increased.

The catheter section (200) shown in FIG. 2 may be made in any of a variety of ways but one acceptable way is this. The inner lubricious tubing (206), the radio-opaque markers (210 & 212), and the inner tubing stiffeners (202 and 204) as well as any associated spacers are placed on a mandrel of an appropriate size. An adhesive such as a thermoplastic may be applied to the outside of this assemblage but desirably is not. A heat shrinkable tubing is placed over the assemblage previously placed on the interior mandrel. The tubing forming the outer tubular layer (208) is then heat shrunk onto the assemblage. It is desirable that the material making up the inner tubing stiffener sections (202 and 204) have a melt temperature in the region of that of the heat shrink temperature of the outer tubular layer (208). This creates a unitary structure having a high kink resistance in addition to the variable flexibility and pushability.

The presence of the comparatively inflexible radio-opaque markers (210 and 212) in the extremely flexible distal section of these catheters represents a challenge in producing a kink resistant device. This challenge is especially difficult when the two (or multi-) marker variation is considered. Under high flexure, the region just adjacent the markers is likely to kink and then bind upon an advancement of the relatively rigid vaso-occlusive devices passed therethrough. This is especially true when the diameter of the vaso-occlusive device is close in size to the inner diameter of the open lumen. We have found that the use of a single layer polymer (often a polyethylene shrinkable tubing) which is sufficiently flexible to function effectively as a distal section for tracking through the cerebral vasculature often is insufficiently strong to maintain its interior shape in the critical region near the radio-opaque marker or markers. Merely increasing the thickness of the layer to alleviate the kinking problem raises the stiffness of the section to potentially unacceptable levels. By combining two layers of tubing materials as described in relationship to FIG. 2 in an overall thickness typically no greater than the thickness of the marker, the goals of enhanced kink resistance, acceptable flexibility (and trackability over a guidewire), and retention of high pushability may be met.

The catheter section of this invention may be coated or otherwise treated both inside and outside to increase their lubricity. Such treatments may include silicone oils or, more preferably, hydrophilic polymers.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that this patent cover those variations as well.

What is claimed is:

1. A catheter section comprising:
    an elongate tubular member having a proximal end and a distal end and a continuous tubular wall extending between those ends, the continuous tubular wall having an inner surface defining an inner lumen extending between those ends, the elongate tubular member comprising:
    a.) at least two segments of inner polymeric stiffener liner comprising LDPE, LLDPE, or mixtures of LLDPE or LDPE with EVA, said at least two segments of inner polymeric stiffener liner having different wall thickness,
    b.) a tubular metallic braid located coaxially about said inner polymeric stiffener liner, said braid having a length,
    c.) an outer tubular cover comprising irradiated and heat-shrunk blend of LLDPE or LDPE with EVA, located coaxially about and in contact with said tubular braid along said length of said braid.

2. The catheter section of claim 1 additionally comprising a distal radio-opaque marker.

3. The catheter section of claim 1 wherein the tubular metallic braid comprises a super-elastic nickle-titanium alloy.

4. The catheter section of claim 1 wherein the tubular metallic braid comprises a stainless steel alloy.

5. The catheter section of claim 1 wherein the outer tubular cover comprises an LDPE blend containing up to 15% EVA.

6. The catheter section of claim 1 further comprising a lubricious layer consisting essentially of FEP and located coaxially within the inner polymeric stiffener liner.

7. The catheter section of claim 1 where at least one of the inner polymeric stiffener liner outer tubular cover comprise materials which are radio-opaque.

8. The catheter section of claim 1 additionally comprising at least one proximal tubular catheter section comprising polymers.

9. The catheter section of claim 8 additionally comprising at least one proximal tubular catheter section consisting essentially of polymers.

* * * * *